United States Patent [19]

Inoue et al.

[11] Patent Number: 5,153,828

[45] Date of Patent: Oct. 6, 1992

[54] BLOOD COLLECTING APPARATUS

[75] Inventors: Satoshi Inoue; Fumiaki Inaba, both of Fujinomiya, Japan

[73] Assignee: Terumo Kabushiki Kaisha, Tokyo, Japan

[21] Appl. No.: 445,536

[22] Filed: Dec. 4, 1989

[30] Foreign Application Priority Data

Dec. 9, 1988 [JP] Japan ................. 63-310197

[51] Int. Cl.$^5$ .............................. G06F 15/00
[52] U.S. Cl. ................. 364/413.07; 128/766; 604/318
[58] Field of Search ........... 364/413.07; 128/760, 128/765, 766, 767, 771; 640/317, 318; 177/188, DIG. 11

[56] References Cited

U.S. PATENT DOCUMENTS

| | | | |
|---|---|---|---|
| 3,698,494 | 10/1972 | Gaudin ................. | 177/118 |
| 3,924,700 | 12/1975 | Lindsey et al. ........ | 177/118 |
| 4,027,735 | 6/1977 | Floyd ................. | 177/118 |
| 4,378,854 | 4/1983 | Rosen ................. | 177/118 |
| 4,390,073 | 6/1983 | Rosen ................. | 177/118 |
| 4,678,049 | 7/1987 | Gunmere et al. ...... | 177/229 |
| 5,010,968 | 4/1991 | Barrow ............... | 177/118 |

Primary Examiner—Roy N. Envall, Jr.
Assistant Examiner—Laura Brutman
Attorney, Agent, or Firm—Frishauf, Holtz, Goodman & Woodward

[57] ABSTRACT

Apparatus for collecting blood includes a control device for starting the action of collecting blood into a continuously or intermittently vibrated blood container, to receive a measured collected blood amount and data of a set amount of blood to be collected into the blood container, and also a vibration stoppage reference time during which the vibration of the blood container is stopped at a blood collection terminating stage so as to calculate, at a midway stage of the blood collection, the amount of blood yet to be collected and the blood collecting speed allowed by the current donor, to calculate, on the basis of the calculated blood collection speed, the yet-to-be-collected blood collecting time that corresponds to the amount of blood yet to be collected. The control device maintains the stoppage of vibration of the blood container on the condition that the yet-to-be-collected blood collecting time has become not more than the vibration stoppage reference time, and causes a stopping of collecting blood into the blood container on the condition that the measured collected blood amount, measured in the stoppage condition, has reached the set blood collection amount.

16 Claims, 7 Drawing Sheets

BLOOD COLLECTING APPARATUS

BACKGROUND OF THE INVENTION

The present invention relates to a blood collecting apparatus.

Blood collecting apparatuses, such as that disclosed in Japanese Patent Publication No. 3153/1976, have been proposed. Conventional blood collecting apparatuses are such that a blood bag is accommodated in a blood collecting chamber, a limit switch detects that the thickness of the blood bag, expanding as blood collection proceeds, has reached a predetermined level, and the blood collecting action is stopped on the basis of this detection, so that a predetermined volume of blood is collected and secured in the blood bag.

Conventional blood collecting apparatuses are also such that a plate supporting the blood bag is swung during the collection of blood into the blood bag, thereby causing blood to be stirred together with an anticoagulant, such as CPD solution (Citrate-Phosphate-Dexture) already charged in the blood bag.

Since it is difficult to accurately measure the amount of collected blood by measuring a change in the thickness of the blood bag, one may consider that, in order to measure the amount of collected blood more accurately, the collected blood amount may be measured by measuring a change in the weight of the blood bag during blood collection.

However, in the case where, during blood collection, a change in the thickness of the blood bag is measured while the blood bag is being vibrated, the exterior configuration of the bag changes as the blood within the blood bag is shaken by the vibration. Accordingly, the thickness of the bag changes not only with changes in the amount of blood collected but also with changes in the angular position of the vibration. For this reason, in order to effect accurate measurement, it is necesssary for the blood bag to be held in its motionless state, and then have its thickness measured at least at the blood collection terminating stage at which the set amount of blood to be collected must be finally reached by the amount of blood collected.

In the case where, during blood collection, a change in the weight of the blood bag is measured while the blood bag is being vibrated, the state in which the weight of the bag applies load on the weight measurement device changes with changes in the angular position of the vibration, thereby making it impossible to perform stable measurement of weight. Also in this case, therefore, in order to effect accurate measurement, it is necessary for the blood bag to be held in its motionless state, and then have its weight measured at least at the blood collection terminating stage at which the set blood collection amount must be finally reached by the amount of collected blood.

Thus, both in the case where the amount of collected blood is measured by detecting a change in the thickness of the blood bag, and in the case where the amount of collected blood is measured on the basis of a change in the weight of the blood bag, it is necessary, at least at the blood collection terminating stage, to effect the measurement of the amount of collected blood while the blood bag is held in its stoppage state. Specifically, when the amount of collected blood has reached a certain amount (hereinafter referred to as "vibration stopping reference amount") at a certain stage before it reaches a set amount of blood to be collected, the vibration of the blood bag is made to remain stopped. The thickness or weight of the blood bag is measured in this stoppage condition.

However, the speed at which blood is collected into the blood bag varies between individual donors. This explains the occurrence of the following cases. When the vibration stopping reference amount is set at a certain value (e.g., when the vibration stopping reference amount is 30 ml while the set amount of blood to be collected is 200 ml), if the donor allows only a low blood collecting speed, the yet-to-be-collected blood collecting time required after the stoppage of blood collection may be as much as several minutes, whereas if the donor allows a high blood collecting speed, the yet-to-be-collected blood collecting time required after the stoppage of blood collection ranges from several seconds to several tens of seconds. In the first case, blood is collected into the blood bag from a donor allowing only a low blood collecting speed, and the blood collection continues in the condition where the vibration of the blood bag remains stopped for a long time. This means that the blood collected is not adequately mixed with an anticoagulant, resulting in the risk of blood coagulation being involved.

The object of the present invention is to provide accurate measurement of blood collected into a blood container, and also to positively prevent of coagulation of collected blood.

SUMMARY OF THE INVENTION

In accordance with the present invention, a blood collecting apparatus for collecting blood into a blood container, comprises blood collecting means; blood collection stopping means; vibrating means for vibrating the blood container; collected blood amount measuring means for measuring the amount of blood collected in the blood container; and control means operable to start the action of collecting blood into the blood container while the blood container is being continuously or intermittently vibrated by the vibrating means, to receive the result of measurement performed by the collected blood amount measuring means and the data of a set amount of blood to be collected into the blood container, and also a vibration stoppage reference time during which the vibration of the blood container is stopped at a blood collection terminating stage so as to calculate, at a midway stage of the blood collection, the amount of blood yet to be collected and the blood collecting speed allowed by the current donor, to calculate, on the basis of the calculated blood collecting speed, the yet-to-be-collected blood collecting time that corresponds to the amount of blood yet to be collected, to maintain the stoppage of the vibration of the blood container by the vibrating means on condition that the yet-to-be-collected blood collecting time has become not more than the vibration stoppage reference time, and to cause the blood collection stopping means to stop the action of collecting blood into the blood container on condition that the result of measurement performed in the stoppage condition by the collected blood amount measuring means has reached the set blood collection amount.

In accordance with a further aspect of the present invention the control means operates in such a manner that the vibration stoppage reference time is set at a time not shorter than the measurement interval of the amount of collected blood between the last measurement time of the same and the next measurement time of the same.

In accordance with a further feature of the present invention, the control means operates in such a manner that the vibration stoppage reference time is set at a time not shorter than the total of the measurement interval of the amount of collected blood and a predetermined additional time.

In accordance with another feature of the present invention the control means operates in such a manner that blood is collected into the blood container while the blood container is being intermittently vibrated by the vibrating means for periods in a predetermined cycle, and also operates in such a manner that a midway measurement of the amount of collected blood is performed while the blood container is temporarily stopped at a specific position in its vibration cycle.

In accordance with yet another feature of the present invention the control means operates in such a manner that the action of the collecting of blood into the blood container is stopped by the blood collection stopping means on condition that the result of measurement performed by the collected blood amount measuring means indicates that the set blood collection amount has been reached, and, thereafter, the blood container is again vibrated by the vibrating means for a certain time, the vibration being stopped thereafter.

In accordance with still another feature of the present invention, input means is provided for allowing the input therethrough of the set amount of blood, and for also allowing the input therethrough of the vibration stoppage reference time.

According to the main features of the present invention, as it is claimed in blood can be collected while the blood container is being vibrated by the vibrating means. At least at the blood collection terminating stage immediately before the amount of collected blood reaches the set blood collection amount, the vibration of the blood container is stopped, and the blood collected therein is measured. Therefore, if the amount of collected blood is measured, e.g., on the basis of a change in the configuration (the thickness, etc.) of the blood container, it is possible to avoid any measurement error due to changes in the configuration of the container resulting from the shaking of blood. If the amount of collected blood is measured, e.g., on the basis of a change in the weight of the blood container, it is possible to avoid any measurement error due to changes in the state in which the weight measurement means is loaded. In either case, it is possible to accurately measure the amount of collected blood.

Also, according to the present invention, it is ascertained that the time required to collect yet-to-be-collected blood in the above-described vibration stoppage condition is not more than a predetermined vibration stoppage reference time, before the collection of blood yet to be collected is effected. With this arrangement, therefore, if a certain time with which there is the risk of blood coagulating due to its inadequate mixing with an anticoagulant within the blood container has previously been determined, and if the vibration stoppage reference time has previously been set at a time shorter than the determined time, it is possible to positively prevent coagulation of blood collected from any donor, without requiring a long stoppage of vibration even in the case of a donor allowing only a low blood collecting speed.

According to another feature of the present invention, it is possible to prevent the amount of collected blood from reaching the set blood collection amount during vibration, and also allowing the final measurement of the amount of collected blood to be invariably effected in the vibration stoppage condition, with accuracy and without involving any excess or shortage. If the measurement interval of the amount of collected blood is, for instance, 4 seconds, and simultaneously if the vibration reference stoppage time is set at 2 seconds shorter than 4 seconds, this results in that, when the yet-to-be-collected blood collecting time resulting from the measurement is 3 seconds exceeding 2 seconds, vibration is again started. In this case, however, 3 seconds or the yet-to-be-collected blood collecting time will be reached, that is, the set amount of blood to be collected will be achieved, before the completion of that subsequent vibration period. Accordingly, when the amount of collected blood will be measured in the next vibration stoppage condition, an amount of collected blood, which is more than the set blood collection amount, will be measured before the termination of the blood collecting action.

According to a further feature of the present invention, in the course of blood collection, the blood container is intermittently vibrated. When a midway measurement of the amount of collected blood is performed while the blood container is temporarily stopped at a specific position in its vibration cycle (e.g., the bottom dead center of the vibration), it is possible to effect an accurate measurement of a midway amount of collected blood in the vibration stoppage condition even though the measurement is performed in the course of the blood collection.

According to yet another feature of the present invention, after the completion of the blood collection, the blood and the anticoagulant are mixed further, thereby making it possible to positively prevent coagulation of blood.

According to still another feature of the present invention, using the input means, it is possible to input the set amount of blood to be collected and the vibration stoppage reference time at request.

DETAILED DESCRIPTION

Figure 1:
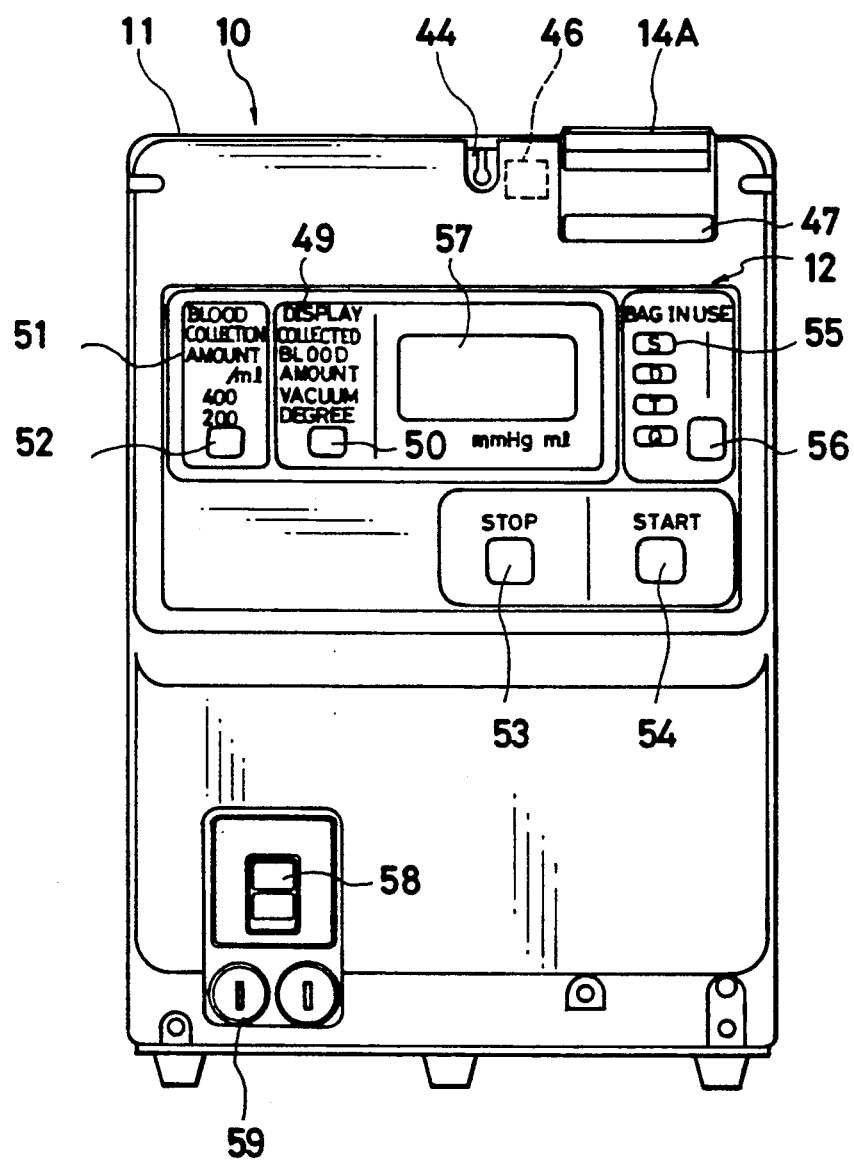
FIG. 1 is a front view showing a blood collecting apparatus in accordance with one embodiment of the present invention.
Figure 2:
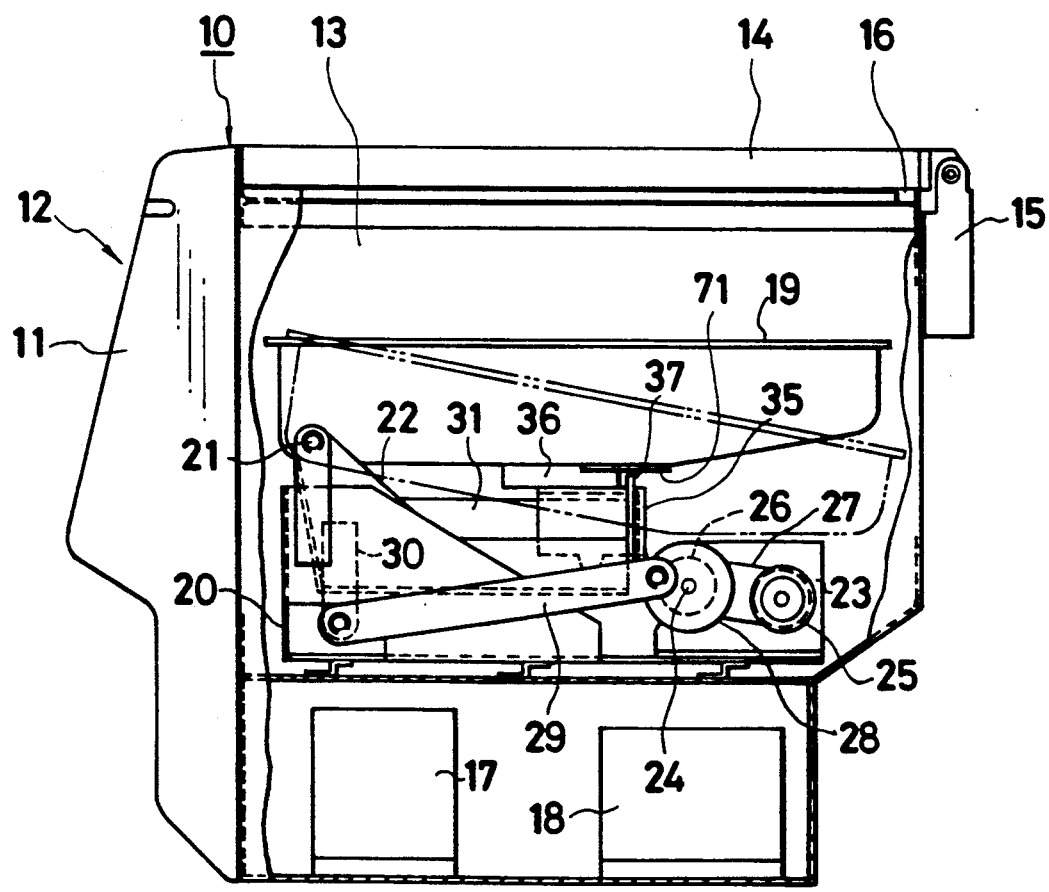
FIG. 2 is a partially cutaway side view showing essential parts of the apparatus shown in FIG. 1.
Figure 3:
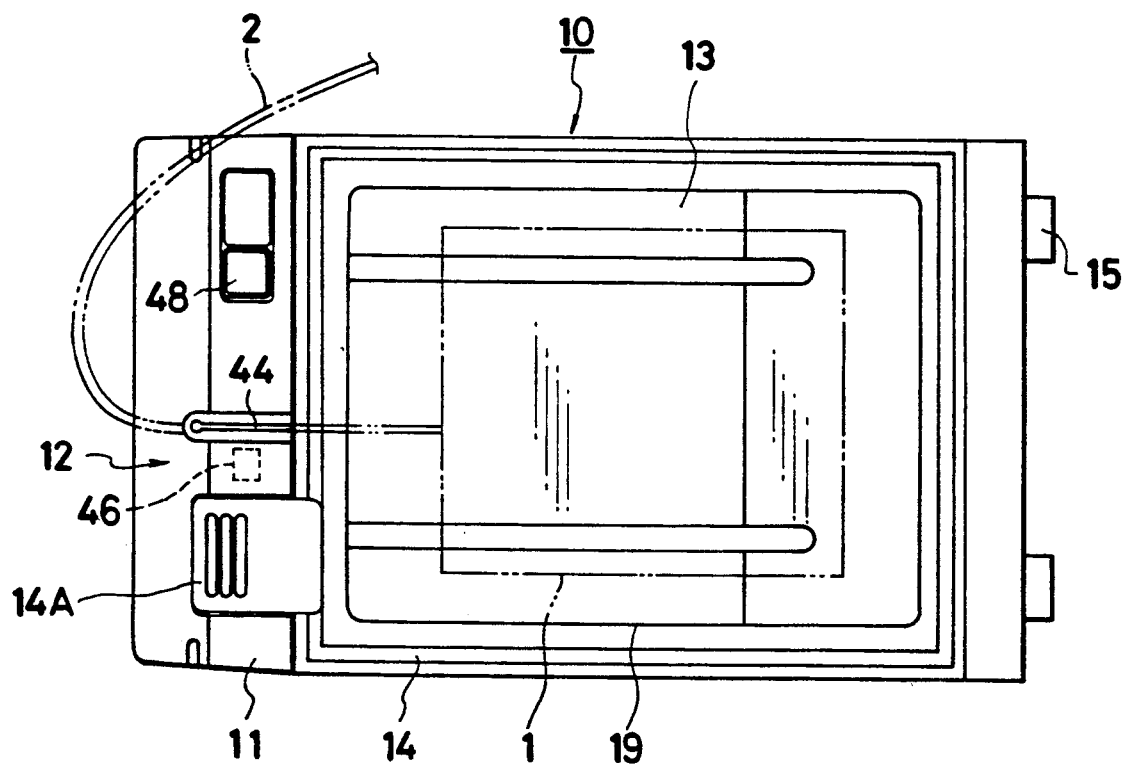
FIG. 3 is a plan view of the apparatus shown in FIG. 1.
Figure 4:
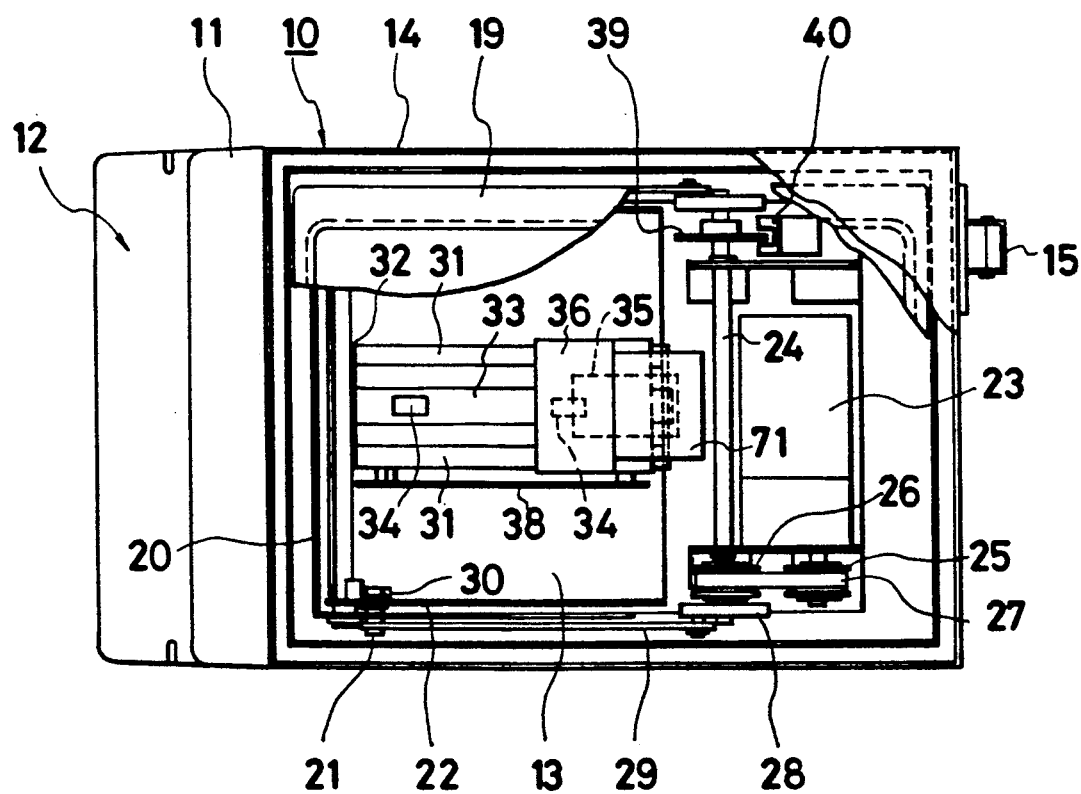
FIG. 4 is a partially cutaway plan view showing essential parts of the apparatus shown in FIG. 1.

As shown in FIGS. 1 to 4, a blood collecting apparatus 10 has a display panel 12 on the front surface of a housing 11, and a blood collecting vacuum chamber 13 formed inside the housing 11. Reference numeral 14 denotes a cover for opening and closing the blood collecting vacuum chamber 13; 15, a hinge for the cover 14; and 16, a sealing rubber for sealing the blood collecting vacuum chamber 13. Reference numeral 14A denotes a handle of the cover 14. The blood collecting apparatus 10 also has a vacuum pump 17 and a control device 18 accommodated within the housing 11 at lower positions thereof.

The blood collecting vacuum chamber 13 of the blood collecting apparatus 10 communicates with a suction port 17A of the vacuum pump 17 so as to enable pressure reduction, and the chamber is provided with a bag supporting plate 19 supporting a blood bag (blood container) 1 formed of polyvinyl chloride or the like. The blood collecting apparatus 10 collects blood while the blood collecting vacuum chamber 13 is in its pressure reduced condition, and while a predetermined negative pressure is applied to the blood bag 1 supported by the bag supporting plate 19. During this time, the blood collecting apparatus 10 operates to swing the bag supporting plate 19 intermittently for periods in a predetermined cycle so as to agitate blood together with an anticoagulant, such as CPD solution, already charged in the blood bag 1, and the apparatus also operates to measure the amount of collected blood by measuring the weight of the blood bag 1.

The structure within the blood collecting apparatus 10 for swinging the above-described bag supporting plate 19 and the structure for measuring the weight of the blood bag 1 within the same are described below.

A base 20 is provided on the bottom of the blood collecting vacuum chamber 13. The base 20 supports, through a supporting shaft 21, a swingable frame 22 capable of swinging. A swinging motor 23 is fixed to the base 20, and a drive shaft 24 driven by the swinging motor 23 is supported by the base 20. Reference numerals 25 and 26 denote toothed pulleys, while reference numeral 27 denotes a toothed belt. A crank wheel 28 is fixed to one end of the drive shaft 24. A link 29 is connected, at one end thereof, to a position on the radius of rotation of the crank wheel 28, the other end of the link 29 being connected to a link piece 30 integral with the swingable frame 22.

Figure 7:
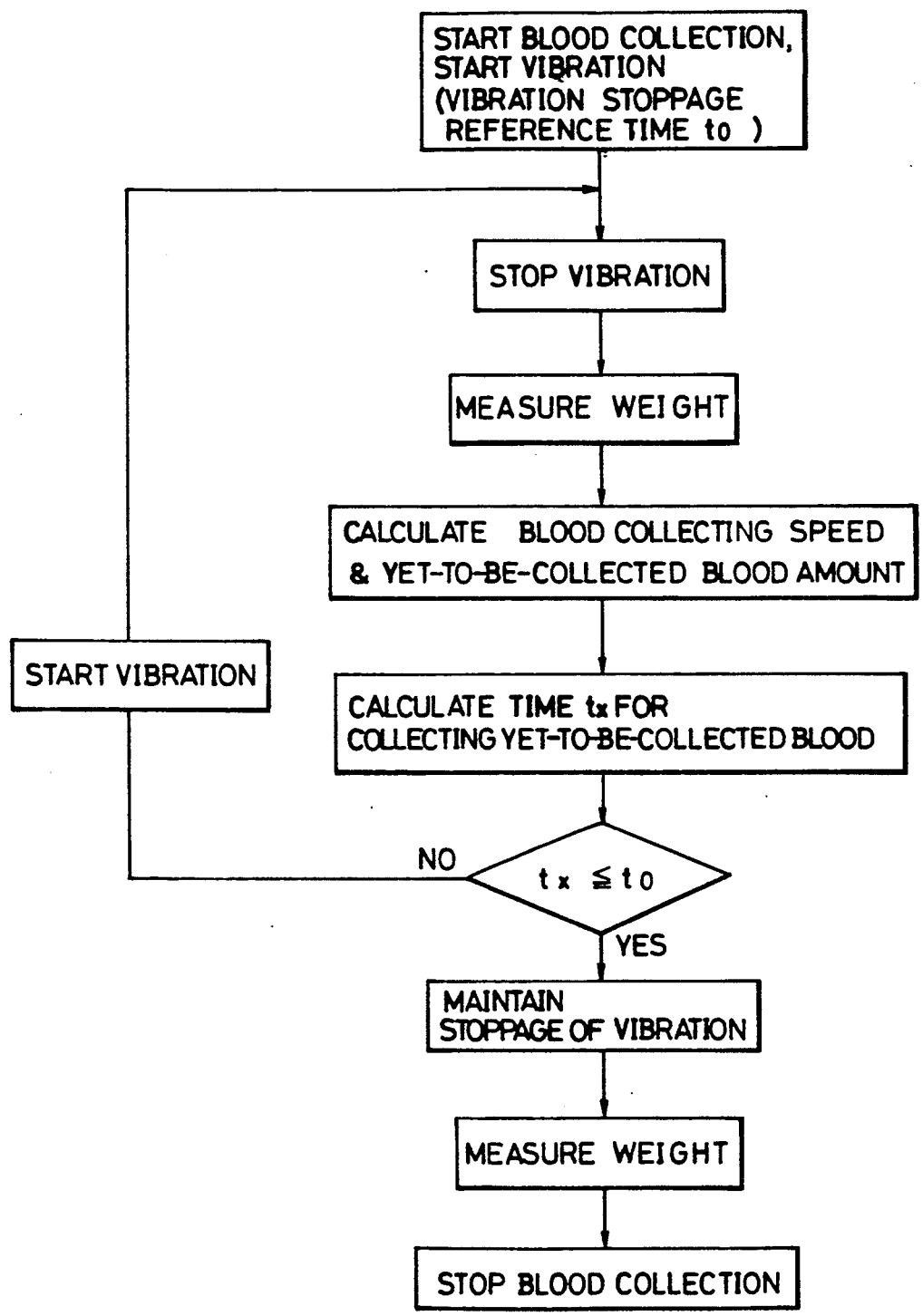
FIG. 7 is a flowchart showing the procedure for the measurement of collected blood amount.

A pair of weighing mounting blocks 31 are fixed to the upper surface of the swingable frame 22, and a weigher (weight measuring means) 33 is cantilevered by a supporting plate 32 disposed across the end portions of these mounting blocks 31. As shown in FIG. 7, the weigher 33 forms a frame-like body which is substantially rectangular (parallelogram-shaped). The weigher 33 is provided with strain gauges 34 which are attached to two positions on the upper surface of the weigher and on two positions on the lower surface of the same in such a manner as to form a Wheatstone bridge circuit, and which serve as a weight sensor. The bag supporting plate 19 is fixed to the tip portion of the weigher 33 through a weighing table 35 and a supporting plate 36. Reference numeral 37 denotes a stopper for preventing lateral vibration of the weigher 33, and reference numeral 38 denotes a weight sensor amplification unit.

With the above-described construction, within the blood collecting apparatus 10, the operation of the swinging motor 23 causes the rotation of the drive shaft 24 and the crank wheel 28, whereby the swingable frame 22 is swung, in turn causing the swinging of the bag supporting plate 19 supported by the swingable frame 22 through the weigher 33. Also within the blood collecting apparatus 10, the bag supporting plate 19 is supported by the weigher 33 cantilevered by the swingable frame 22 through the mounting blocks 31 and the supporting plate 32, whereby the weight of the blood bag 1 is measured on the basis of change in the output of the strain gauges 34 in response to the flexural deformation of the weigher 33, so as to measure the amount of collected blood.

The blood collecting apparatus 10 also has the following arrangement. The rotational position of a detection cam 39 provided at the second end of the drive shaft 24 is detected by an optical sensor 40, so as to control the driving of the swinging motor 23. This allows the bag supporting plate 19 to be temporarily stopped at its lowermost descent point (the bottom dead center) and be held in its state of maintaining a certain attitude, in which condition, the weight of the blood bag 1 is measured in the above described manner.

Figure 5:
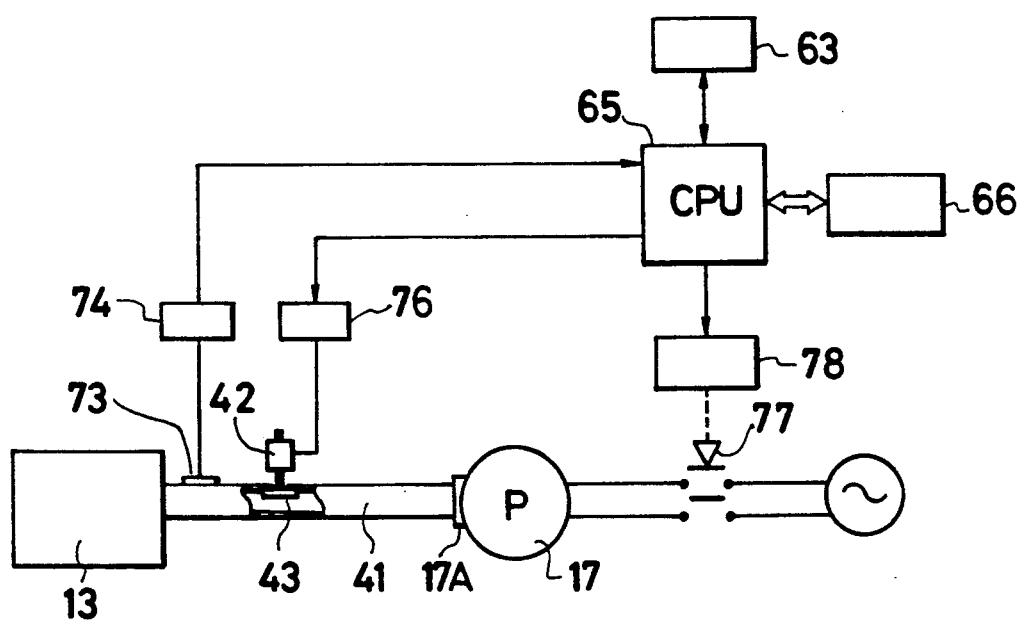
FIG. 5 is a view of a vacuum circuit.

As shown in FIG. 5, within the blood collecting apparatus 10, the suction port 17A of the vacuum pump 17 is connected to the blood collecting vacuum chamber 13 via a vacuum pipe 41. A solenoid valve 43 is provided at an intermediate portion of the vacuum pipe 41, which valve closes when an evacuation solenoid 42 is energized, whereas it opens under weight when the evacuation solenoid 42 is deenergized. The blood collecting apparatus 10 performs the on/off control of the vacuum pump 17 so as to form a certain negative pressure (a certain degree of vacuum) within the blood collecting vacuum chamber 13. At the completion of blood collection, the evacuation valve 43 is opened, thereby opening the blood collecting vacuum chamber 13 to the atmosphere.

The blood collecting apparatus 10 further includes a tube holder 44 on a front-side upper portion of the housing 11 which is adjacent to the blood collecting vacuum chamber 13, so as to enable the pulling out a blood collecting tube 2 communicating with the blood bag 1 accommodated in the blood collecting vacuum chamber 13. The tube holder 44 is provided with a tube clamp (blood collection stopping means) 46 driven by a tube clamp solenoid 45. The tube clamp 46 is operable to clamp and press on the blood collecting tube 2 until the tube is closed so as to stop the action of collecting blood into the blood bag 1. Reference numeral 47 denotes a clamp release button for the tube clamp 46, and reference numeral 48 denotes a clamp button for actuating the tube clamp 46 in emergency.

The display panel 12 of the blood collecting apparatus 10 has a lamp 49 for switchingly displaying the collected blood amount/vacuum degree, a collected blood amount/vacuum degree selection switch 50, a lamp 51 for switchingly displaying 400 ml/200 ml, a 400 ml/200 ml selection switch 52, a stop switch 53, a start switch 54, a lamp 55 for displaying the bag in use, a bag-in-use selection switch 56, and a portion 57 for displaying the collected blood amount/vacuum degree. The blood collecting apparatus 10 further includes a power switch 58 and a fuse holder 59 which are at lower portions on the front surface of the housing 11, as well as a power source connector 60 at a lower portion on the reverse surface of the housing 11.

Figure 6:
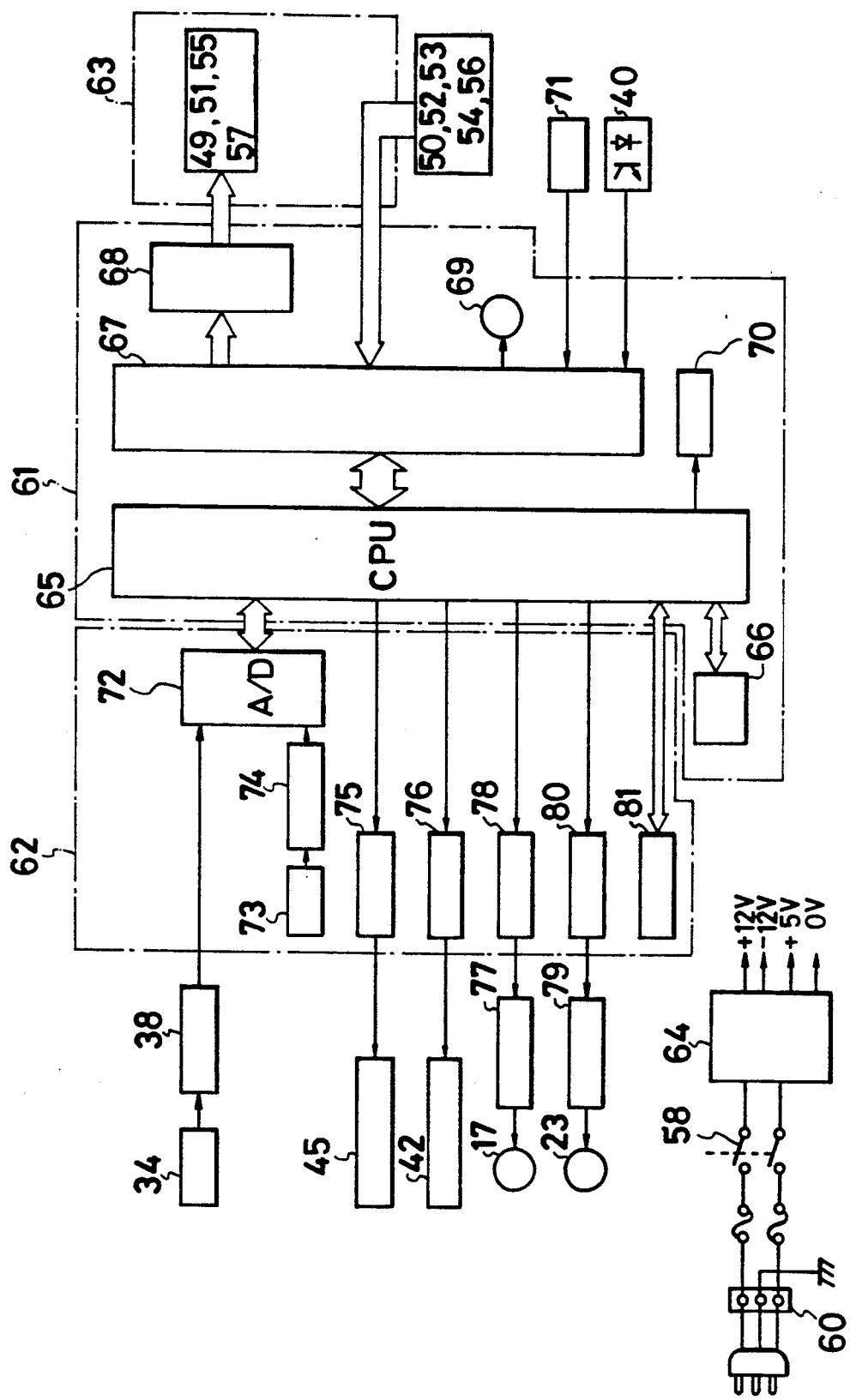
FIG. 6 is a control block diagram.

Next, a description will be given of the control device 18 of the blood collecting apparatus 10. As shown in FIG. 6, the control device 18 mainly comprises a main control circuit 61, a drive circuit 62, and a display circuit 63. Denoted by 64 is a power source unit.

The main control circuit 61 has a CPU (central processing unit) [including a memory into which a control program for effecting a series of operations of the apparatus 10 is written] 65, a memory (storing means) 66, an input/output control section 67, an LED (light emitting diode) drive circuit 68, a buzzer 69, and a fail-safe circuit 70. Detection signals from the above-mentioned optical sensor 40 for detecting the swinging position of the bag supporting plate 19 and from a blood leakage sensor 71 for detecting leakage of blood from the blood bag 1 are transmitted to the input/output control section 67.

The above-mentioned memory 66 comprises a non-volatile memory such as an EA-ROM or EEP-ROM, and it allows the rewriting and the reading of stored data, while being capable of holding stored data without any application thereon of power source voltage. The memory 66 stores data such as ① the negative pressure to be generated in the blood collecting vacuum chamber 13, ② the set amount of blood to be collected into the blood bag 1, ③ the reference time during which the vibration of the blood bag 1 is to be stopped at the blood collection terminating stage, and ④ the time during which the bag supporting plate 19 (the blood bag 1) is again swung after the completion of the blood collection.

The buzzer 69 generates sounds in one of different sound-generating manners in accordance with, e.g., ① the completion of blood collection, ② the occurrence of error in the negative pressure generated in the blood collecting vacuum chamber 13, ③ the occurrence of error in the rotation of the swinging motor 23, and ④ the detection of blood leakage by the blood leakage sensor 71.

The fail-safe circuit 70 checks the occurrence of runaway of the CPU 65, and, at the time of runaway, stops the apparatus in its safe condition.

The drive circuit 62 is connected to the main control circuit 61, and it has an A/D conversion circuit 72. The weight sensor amplification unit 38, to which the above-described strain gauges 34 are connected, is connected to the A/D conversion circuit 72. A pressure sensor 73 provided in the above-described vacuum pipe 41 in order to detect the negative pressure within the blood collecting vacuum chamber 13 is connected to the A/D conversion circuit via a pressure sensor amplification circuit 74.

With this arrangement, the CPU 65 of the control device 18 calculates the weight of collected blood on the assumption that the output y of the strain gauges 34 is in a certain relationship with the measured weight w of collected blood, which can be expressed as the linear function $y = aw + b$. Also, on the assumption that the output z of the pressure sensor 73 is in a certain relationship with the measured pressure p, which can be expressed as the linear function $z = cp + d$, the CPU 65 calculates this pressure.

The drive circuit 62 also has ① a solenoid drive circuit 75 for controlling the tube clamp solenoid 45, ② a solenoid drive circuit 76 for controlling the evacuation solenoid 42, ③ a pump drive circuit 78 for turning on/off a power supply switch 77 for the vacuum pump 17, and ④ a motor drive circuit 80 for turning on/off a power supply switch 79 for the swinging motor 23.

The CPU 65 of the control device 18 receives the detection output of the pressure sensor 73 and the set pressure within the blood collecting vacuum chamber 13, which is among data stored in the memory 66, and it on/off controls the power supply switch 77 for the vacuum pump 17, as stated before, in such a manner that detected pressure coincides with the set pressure. This operation causes the negative pressure within the blood collecting vacuum chamber 13 to undergo fine changes within a fixed range of the set pressure, so that, as a result, a constant pressure condition is achieved.

Next, a description will be given of the procedure for the blood collecting operation performed by the blood collecting apparatus 10 (with reference to FIG. 7)

① The power switch 58 is turned on.

② The amount of blood to be collected is selected by means of the 400 ml/200 ml selection switch 52. The result of this selection is displayed by the switchingly displaying lamp 51.

③ The bag to be used is selected by means of the bag-in-use selection switch 56. The result of this selection is displayed by the display lamp 55. The bag in use may be one of the following types: the single (S) type solely comprising the main bag, and types further comprising at least one small bag, i.e., the double (D) type, the triple (T) type, and the quadruple (Q) type ④ A blood collecting needle provided at the tip of the blood collecting tube 2 is stuck into the donor, and this is followed by the collection of blood to a certain extent.

⑤ The blood collecting bag 1 is received in the blood collecting vacuum chamber 13 and is placed on the bag supporting plate 19. The blood collecting tube 2 is set in the tube holder 44. The cover 14 is shut.

⑥ The start switch 54 is turned on. The control device 18 controls the driving of the vacuum pump 17 and the swinging motor 23 in such a manner that blood is collected with pressure reduction in the blood collecting vacuum chamber 13, while the bag supporting plate 19 is swung. The control device 18 also operates, at a midway stage of the blood collection, at a timing at which the bag supporting plate 19 temporarily stops at its lowermost descent point, to receive the output of the weight sensor amplification unit 38, detect the measured amount of blood collected in the blood bag 1, and calculate the amount (volume) of blood yet to be collected, by using the set blood collection amount, the specific gravity of blood, and the previously-registered weight of the blood bag 1, these data being written in the memory 66, and using the following equation (1):

$$\text{Yet-to-be-collected blood amount (ml)} = \frac{[\text{set blood collection amount (g)} + \text{previously-registered weight (g)} - \text{collected blood measured amount (g)}]}{\text{specific gravity (g/ml)}} \quad (1)$$

Also at the midway stage of blood collection, the control device 18 calculates the blood collecting speed allowed by the current donor, and it also calculates, from the resultant blood collecting speed, the yet-to-be-collected blood collecting time that corresponds to the above-mentioned yet-to-be collected blood amount.

⑦ On condition that the yet-to-be-collected blood collecting time resulting from the above-described calculation has become not more than the vibration stoppage reference time written in the memory 66, the control device 18 controls the driving of the swinging motor 23 in such a manner that the swinging of the bag supporting plate 19 remains stopped.

During the vibration stoppage condition, the control device 18 calculates, in a manner similar to that described under Item ⑥, the amount of blood yet to be collected during this final stage of blood collection. Then, on condition that this yet-to-be-collected blood amount has reached zero, the control devices causes the tube clamp 46 to close the blood collecting tube 2, thereby stopping the acting of collecting blood into the blood bag 1. At this time, the control device 18 stops the vacuum pump 17, and it also opens the evacuation valve 43 so as to open the blood collecting vacuum chamber 13 to the atmosphere.

(8) After the completion of the above-described blood collection, the control device 18 causes a re-driving of the swinging motor 23 for a certain time, so as to again swing the bag supporting plate 19. Thereafter, the buzzer posts the completion of blood collection.

(9) The clamp release button 47 is turned on, the cover 14 is opened, the blood collecting tube 2 is removed from the tube holder 44, and the blood collecting bag 1 is taken out of the blood collecting vacuum chamber 13.

Next, the operation of the above-described embodiment will be explained.

With the above-described embodiment, blood can be collected while the blood collecting bag 1 is being vibrated by the swinging motor 23. Furthermore, the weight of blood collected therein is measured while the blood bag 1 is temporarily stopped at a specific position in its vibration cycle. By virtue of this arrangement, the amount of collected blood is measured on the basis of the measurement of change in the weight of the blood bag 1, hence, is measured at a high level of precision. Furthermore, since the blood bag 1 and the bag supporting plate 19 are stopped at their specific positions during the measurement of weight, their state of applying load on the weigher 33 is always the same, thereby ensuring stable measurement of the weight of collected blood. In brief, during the collection of blood in which the blood bag 1 is being vibrated, the level of precision with which the collected blood amount is measured can be secured at an improved level.

In the above-described embodiment, it is ascertained that the time required to collect yet-to-be-collected blood in the vibration stoppage condition of the blood bag 1 is not more than a predetermined vibration stoppage reference time, before the collection of blood yet to be collected is effected. Therefore, with a certain time with which there is the risk of blood coagulating due to its inadequate mixing with an anticoagulant with the blood bag 1 having previously been determined, and with the vibration reference time having previously been set at a time shorter than the determined time, it is possible to positively prevent coagulation of blood collected from any donor, without requiring a long stoppage of vibration even in the case of a donor allowing only a low blood-collecting speed.

In the above-described embodiment, with the vibration stoppage reference time being set at a time not shorter than the total of the measurement interval of the amount of collected blood and a certain additional time, it is possible to prevent the amount of collected blood from reaching the set blood collection amount during vibration, while allowing the final measurement of the amount of collected blood to be invariably effected in the vibration stoppage condition, with accuracy and without involving any excess or shortage. The above measurement interval of the amount of collected blood means the interval between the last measurement time of the same and the next measurement time of the same. This advantage will be explained in detail. If one vibration period is, for instance, 4 seconds, and simultaneously if the vibration stoppage reference time is set at 2 seconds shorter than 4 seconds, this results in that, when the yet-to-be-collected blood collecting time resulting from the midway measurement is 3 seconds exceeding 2 seconds, vibration is again started. In this case, however, 3 seconds or the yet-to-be-collected blood collecting time will be reached, that is, the set amount of blood to be collected will be achieved, before the completion of that subsequent vibration period. Accordingly, when the amount of collected blood will be measured in the next vibration stoppage condition, an amount of collected blood, which is more than the amount that should be measured by the control device 18, before the termination of the blood collecting action. In contrast, if the vibration stoppage reference time is set at 6 seconds which is the total of 4 seconds, the above-described one vibration period, and a certain additional time, this makes it possible to avoid such inconvenience as that described above, i.e., the collection of excessive amount of blood.

With the above-described embodiment, after the completion of the collection of the set amount of blood, the swinging motor 23 is driven so as to again swing the bag supporting plate 19, whereby the blood and the anticoagulant are mixed further. This makes it possible to positively prevent coagulation of blood.

With the above-described embodiment, using the memory 66 and the input/output control section 67, it is possible to input the desired set amount of blood to be collected and the desired vibration stoppage reference time.

In carrying out the present invention, the vibrating means used may be the means that continuously vibrates the blood container in the course of blood collection.

Also in carrying out the present invention, the collected blood amount measuring means used may be the means that does not measure the amount of collected blood on the basis of the weight of the blood container, but measures the same by measuring change in the configuration (thickness, etc.) of the blood container which occurs as blood collection proceeds.

Also in carrying out the present invention, the vibration stoppage reference time may be set at a time not shorter than the measurement interval of the amount of collected blood between the last measurement time of the same and the next measurement time of the same.

As has been described above, according to the present invention, it is possible to accurately measure the amount of blood collected into the blood container, while making it possible to positively prevent coagulation of collected blood.

What is claimed is:

1. A blood collecting apparatus for collecting blood into a blood container, comprising:
   blood collecting means;
   blood collection stopping means;
   vibrating means for vibrating said blood container;
   collected blood amount measuring means for measuring the amount of blood collected in said blood container; and
   control means for starting collecting of blood into said blood container while said blood container is being vibrated by said vibrating means, for receiving the result of measurement performed by said collected blood amount measuring means and data of a set amount of blood to be collected into said blood container, and for receiving a vibration stoppage reference time during which the vibration of said blood container is stopped at a blood collection terminating stage, said control means including:
- means for setting the vibration stoppage reference time at a time not shorter than a measurement interval of an amount of collected blood between a last measurement time of the amount of collected blood and a next measurement time of the amount of collected blood;
- a means for calculating, at a midway stage of the blood collection, an amount of blood yet to be collected and a blood collecting speed allowed by a current donor;
- means for calculating, on the basis of the calculated blood collecting speed, a yet-to-be-collected blood collecting time that corresponds to an amount of blood yet to be collected;
- means for maintaining stoppage of vibration of said blood container by said vibrating means when a yet-to-be-collected blood collecting time has become not more than the vibration stoppage reference time; and
- means for causing said blood collection stopping means to stop the action of collecting blood into said blood container when the result of measurement performed in the stoppage condition by said collected blood amount measuring means has reached a set blood collection amount.

2. A blood collecting apparatus according to claim 1, wherein said control means further includes setting means for setting the vibration stoppage reference time at a time not shorter than a measurement interval of an amount of collected blood between a last measurement time of the amount of collected blood and a next measurement time of the amount of collected blood.

3. A blood collecting apparatus according to claim 2, wherein said setting means includes means for setting the vibration stoppage reference time at a time not shorter than the total of the measurement interval of the amount of collected blood and a predetermined additional time.

4. A blood collecting apparatus according to claim 3, wherein said control means permits blood to be collected into said blood container while said blood container is being intermittently vibrated by said vibrating means for periods in a predetermined cycle, and includes means for enabling a midway measurement of the amount of collected blood while said blood container is temporarily stopped at a specific position in its vibration cycle.

5. A blood collecting apparatus according to claim 3, wherein said control means includes means for stopping said collecting of blood into said blood container by said blood collection stopping means when a result of measurement performed by said collected blood amount measuring means indicates that a set blood collection amount has been reached, and, thereafter, for enabling said blood container to again be vibrated by said vibrating means for a certain time, the vibration being stopped after elapsing of said certain time.

6. A blood collecting apparatus according to claim 3 further comprising input means for allowing the input therethrough of a set amount of blood, and for also allowing the input therethrough of said vibration stoppage reference time.

7. A blood collecting apparatus according to claim 2, wherein said control means permits blood to be collected into said blood container while said blood container is being intermittently vibrated by said vibrating means for periods in a predetermined cycle, and includes means for enabling a midway measurement of the amount of collected blood while said blood container is temporarily stopped at a specific position in its vibration cycle.

8. A blood collecting apparatus according to claim 2, wherein said control means includes means for stopping said collecting of blood into said blood container by said blood collection stopping means when a result of measurement performed by said collected blood amount measuring means indicates that a set blood collection amount has been reached, and, thereafter, for enabling said blood container to again be vibrated by said vibrating means for a certain time, the vibration being stopped after elapsing of said certain time.

9. A blood collecting apparatus according to claim 2 further comprising input means for allowing the input therethrough of a set amount of blood, and for also allowing the input therethrough of said vibration stoppage reference time.

10. A blood collecting apparatus according to claim 1, wherein said control means permits blood to be collected into said blood container while said blood container is being intermittently vibrated by said vibrating means for periods in a predetermined cycle, and includes means for enabling a midway measurement of the amount of collected blood while said blood container is temporarily stopped at a specific position in its vibration cycle.

11. A blood collecting apparatus according to claim 1, wherein said control means includes means for stopping said collecting of blood into said blood container by said blood collection stopping means when a result of measurement performed by said collected blood amount measuring means indicates that a set blood collection amount has been reached, and, thereafter, for enabling said blood container to again be vibrated by said vibrating means for a certain time, the vibration being stopped after elapsing of said certain time.

12. A blood collecting apparatus according to claim 11, wherein said control means permits blood to be collected into said blood container while said blood container is being intermittently vibrated by said vibrating means for periods in a predetermined cycle, and includes means for enabling a midway measurement of the amount of collected blood while said blood container is temporarily stopped at a specific position in its vibration cycle.

13. A blood collecting apparatus according to claim 1 further comprising input means for allowing the input therethrough of a set amount of blood, and for also allowing the input therethrough of said vibration stoppage reference time.

14. A blood collecting apparatus according to claim 13, wherein said control means permits blood to be collected into said blood container while said blood container is being intermittently vibrated by said vibrating means for periods in a predetermined cycle, and includes means for enabling a midway measurement of the amount of collected blood while said blood container is temporarily stopped at a specific position in its vibration cycle.

15. A blood collecting apparatus according to claim 14, wherein said control means includes means for stopping said collecting of blood into said blood container by said blood collection stopping means when a result of measurement performed by said collected blood amount measuring means indicates that a set blood collection amount has been reached, and, thereafter, for enabling said blood container to again be vibrated by said vibrating means for a certain time, the vibration being stopped after elapsing of said certain time.

16. A blood collecting apparatus according to claim 13, wherein saic control means includes means for stopping said collecting of blood into said blood container by said blood collection stopping means when a result of measurement performed by said collected blood amount measuring means indicates that a set blood collection amount has been reached, and, thereafter, for enabling said blood container to again be vibrated by said vibrating means for a certain time, the vibration being stopped after elapsing of said certain time.

* * * * *

UNITED STATES PATENT AND TRADEMARK OFFICE
CERTIFICATE OF CORRECTION

PATENT NO. : 5,153,828
DATED : October 6, 1992
INVENTOR(S) : INOUE et al

It is certified that error appears in the above-identified patent and that said Letters Patent is hereby corrected as shown below:

Column 2, line 28, following "prevent", delete "of".

Column 3, line 34, delete "as it is claimed in".

Signed and Sealed this

Thirtieth Day of November, 1993

Attest:

BRUCE LEHMAN

Attesting Officer          Commissioner of Patents and Trademarks